US00PP35750P2

(12) United States Plant Patent
Yanny et al.

(10) Patent No.: US PP35,750 P2
(45) Date of Patent: Apr. 16, 2024

(54) ***BUXUS* PLANT NAMED 'JN SELECT I'**

(50) Latin Name: ***Buxus* hybrid**
Varietal Denomination: JN Select I

(71) Applicants: JN Plant Selections, LLC, Milwaukee, WI (US); Saunders Genetics, LLC, Piney River, VA (US)

(72) Inventors: Michael D. Yanny, Milwaukee, WI (US); Lori K Yanny, Milwaukee, WI (US)

(73) Assignees: JN PLANT SELECTIONS, LLC, Milwaukee, WI (US), part interest; SAUNDERS GENETICS, LLC, Piney River, VA (US), part interest ( * ) Notice: Subject to any disclaimer, the term of this patent is extended or adjusted under 35 U.S.C. 154(b) by 0 days.

(21) Appl. No.: 18/235,410

(22) Filed: Aug. 18, 2023

(51) Int. Cl.
*A01H 5/00* (2018.01)
*A01H 6/00* (2018.01)

(52) U.S. Cl.
USPC ..... Plt./226

(58) Field of Classification Search
USPC ..... Plt./226
See application file for complete search history.

*Primary Examiner* — Susan McCormick Ewoldt
(74) *Attorney, Agent, or Firm* — Penny J. Aguirre

(57) ABSTRACT

A new cultivar of *Buxus* plant named 'JN Select I' that is characterized by its slightly tall height with a wide globe plant form with minimal shearing each year, its foliage that is very glossy and dark green in color during the growing season with the dark green foliage color retained in winter when provided shade, its very good cold hardiness with hardiness at least to U.S.D.A. Zone 4, and its high resistance to boxwood blight.

2 Drawing Sheets

Botanical classification: *Buxus* hybrid.
Variety denomination: 'JN Select I'.

BACKGROUND OF THE INVENTION

The present invention relates to a new and distinct cultivar of *Buxus* of hybrid origin and will be referred to hereafter by its cultivar name, 'JN Select I'. 'JN Select I' is a new cultivar of boxwood grown for use as an ornamental landscape plant.

The new cultivar was developed from an ongoing breeding program conducted by the Inventors in Menomonee Falls, Wisconsin. The goal of the breeding program was to select new cultivars of *Buxus* with improved hardiness in the upper Midwest, high resistance to box blight, ease to propagate and produce, winter color, plant form, density and foliage quality. 'JN Select I' arose as a seedling of open pollination in 1989, 1990, and 1991 of various plants that were hybrids of *Buxus sinica* var. *insularis* and *Buxus sempervirens*; including 'Green Mound' (unpatented), 'Green Velvet' (unpatented), and other unnamed and unpatented plants from the Inventors' breeding program. The collected seeds were pooled prior to planting for evaluation; therefore, the exact parentage of the new cultivar is unknown. The Inventors' selected the new cultivar as a single unique plant from amongst the seedlings of the above crosses in July of 2001 followed by many years of testing for cold hardiness and boxwood blight to insure superior characteristics.

Asexual propagation of the new cultivar was first accomplished by one of the Inventors by stem cuttings in July of 2001 in Menomonee Falls, Wisconsin. Asexual propagation of the new cultivar by stem cuttings has determined that the characteristics are stable and are reproduced true to type in successive generations.

SUMMARY OF THE INVENTION

The following traits have been repeatedly observed and represent the characteristics of the new cultivar. These attributes in combination distinguish 'JN Select I' as a unique cultivar of *Buxus*.

1. 'JN Select I' exhibits a slightly tall height with a wide globe plant form with minimal shearing each year.
2. 'JN Select I' exhibits foliage that is very glossy and dark green in color during the growing season with the dark green foliage color retained in winter when provided shade.
3. 'JN Select I' exhibits very good cold hardiness with hardiness at least to U.S.D.A. Zone 4.
4. 'JN Select I' exhibits high resistance to boxwood blight.

'JN Select I' can be most closely compared to the *Buxus* cultivars 'Green Gem' (not patented), 'Green Velvet', and 'Green Mound'. 'Green Gem' is similar to 'JN Select I' in having a globe plant form and small leaves that are dark green in color. 'Green Gem' differs from 'JN Select I' in having leaves that are less glossy, a slightly less dense plant habit and less resistance to boxwood blight. 'Green Velvet' is similar to 'JN Select I' in having a mounded, globe plant form and leaves that are glossy and dark green in color. 'Green Velvet' differs from 'JN Select I' in having leaves that are larger in size, less resistance to boxwood blight, and less cold hardiness. 'Green Mound' differs from 'JN Select I' in having less cold hardiness and less resistance to boxwood blight.

BRIEF DESCRIPTION OF THE DRAWINGS

The accompanying color photographs illustrate the overall appearance and distinct characteristics of the new *Buxus*.

The photographs were taken of a 17-year-old plant as grown outdoors in a trial plot in Menomonee Falls, Wisconsin.

Figure 1:
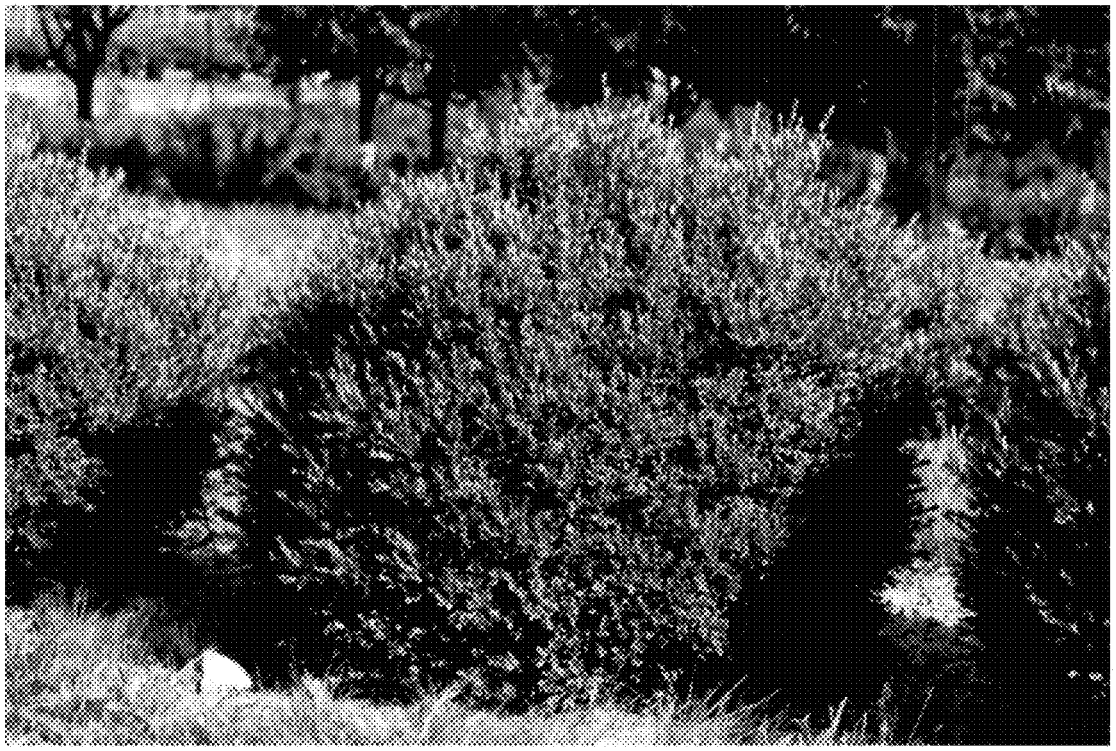

The photograph in FIG. 1 provides a side view of the plant habit of 'JN Select I' (with a light shearing annually when young).

Figure 2:
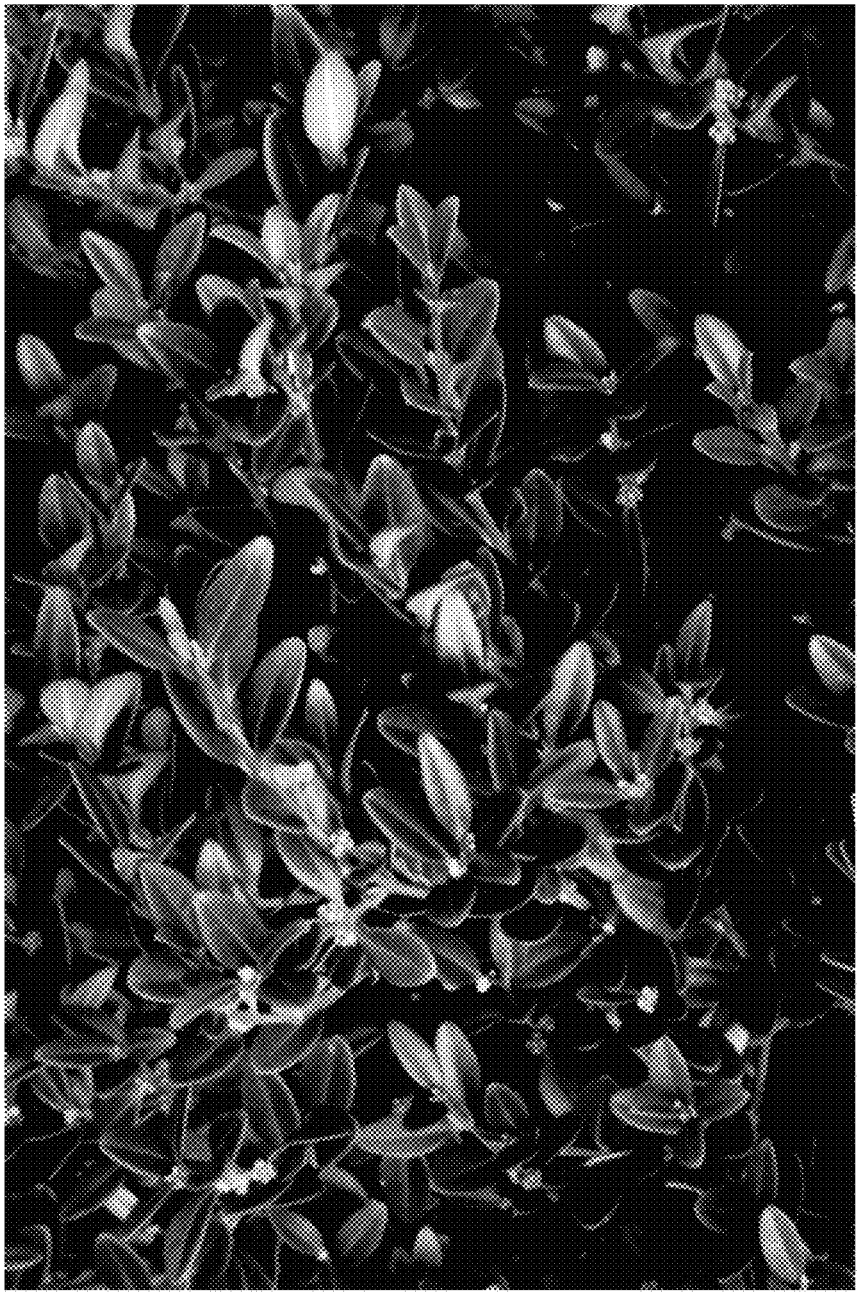

The photograph in FIG. 2 provides a close-up view of the foliage of 'JN Select I'.

The colors in the photographs are as close as possible with the photographic and printing technology utilized and the color values cited in the detailed botanical description accurately describe the colors of the new *Buxus*.

DETAILED BOTANICAL DESCRIPTION

The following is a description of 3-year-old plants as grown outdoors in quart containers in Menomonee Falls, Wisconsin. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—Typically 1 to 2 weeks in early to mid-April in south east Wisconsin, dependent on weather.

*Plant type*.—Evergreen shrub.

*Plant habit*.—Dense, bushy, tall globe with light shearing annually when young (a wide pyramidal shape is attained without shearing).

*Height and spread*.—3-year-old plant average is 14 cm in height, 9 cm in width, a 17-year-old plant will grow to about 91 cm tall by 81 cm in width with a light shear annually when young when grown in Southeast Wisconsin, without any shearing the plants become a fat pyramid.

*Cold hardiness*.—At least to U.S.D.A. Zone 4.

*Diseases resistance*.—Highly resistant to boxwood blight (caused by *Calonectria pseudonaviculata*).

*Root description*.—Fibrous and fine, moderately dense, 163C and 164D in color.

*Propagation*.—Stem cuttings.

*Root development*.—Cutting taken in July initiates roots in 8 to 10 weeks and are fully rooted by October and after overwintering and planted in a 3-inch liner in spring will fully root by fall.

*Growth rate*.—Moderate, 8 cm to 10 cm of growth/year.

Stem description:

*Shape*.—Quadrangular.

*Stem color*.—Young stems; 144A, mature stems; a blend of 144A and 199A and 163D, trunk; a blend of 199A and 161D.

*Stem size*.—Main stems; 4 cm in length and 5 mm in diameter, lateral stems; 14 cm in length and 2 mm in diameter, tertiary branches; 3.5 cm in length and 1 mm in diameter.

*Stem strength*.—Main and lateral stems; strong, tertiary stems; moderately strong, bendable.

*Stem arrangement*.—Lateral stems are opposite and whorled up main branch.

*Stem aspect*.—Upright, held in a 30° to vertical (vertical =0°).

*Stem surface*.—Young stems; glabrous, glossy, mature stems and trunk; rugose, dull, bark-like.

*Branch number*.—Main stem; 1, lateral stems; 8, tertiary stems; 12.

*Branching habit*.—Dense, held in multiple angles from main stem.

Foliage description:

*Leaf shape*.—Elliptic, sometimes slightly lanceolate.

*Leaf division*.—Simple.

*Leaf base*.—Cuneate-attenuate.

*Leaf apex*.—Broadly acute.

*Leaf fragrance*.—Light fresh fragrance.

*Leaf venation*.—Pinnate, midrib; upper surface 137B, lower surface 138D, other veins matching leaf color.

*Leaf margins*.—Entire.

*Leaf arrangement*.—Opposite.

*Leaf attachment*.—Petiolate.

*Internode length*.—Up to 1 cm.

*Leaf surface*.—Glabrous and shiny on upper surface, glabrous and matt on lower surface with midrib densely pubescent with very short hairs.

*Leaf texture*.—Slightly thick, tough and waxy.

*Leaf size*.—An average of 1.8 cm in length and 8mm in width.

*Leaf quantity*.—Average of 35 on a secondary branch (including tertiary branches) 10 cm in length.

*Leaf color*.—Young; 144B on upper and lower surface, mature; upper surface 137A, lower surface; N189A with thin margin 139A.

*Petioles*.—Up to 2.5 mm in length and 1 mm in width, both surfaces 138B in color and glabrous.

Inflorescence description:

*Inflorescence*.—Arranged in dense clusters (aggregate) of single flowers at upper leaf axils of secondary and tertiary branches, monoecious, primarily male flowers.

*Inflorescence size*.—Average of 1.1 cm in width, 7 mm in height.

*Significance*.—Flowers are insignificant and non-showy.

*Lastingness of inflorescence*.—Average of one week.

*Inflorescence fragrance*.—Moderate acidic scent.

*Flower buds*.—Clusters; round in shape, 4 mm in diameter and length, individual buds; oval in shape, 2 mm in diameter and 2.5 mm length, surface glabrous, color 162D and 144A.

*Flower number*.—12 to 20 male flowers and 1 female flower per inflorescence, average of 12 inflorescences per secondary branch 15 cm in length.

*Flower size*.—Male flowers an average of 5 mm in length and 4 mm in width, female flowers an average of 4 mm in length and 3 mm in width.

*Petals*.—Apetalous.

*Sepals* (*sometime referred to as tepals*).—4 on male flowers, 6 on female flowers, imbricate, about 3.5 mm in length and 1.5 to 2 mm in width, glabrous surface, cuneate and fused base, acute apex, margins entire, 144A in color with translucent margins.

*Peduncles*.—None, sessile to node.

Reproductive organs:

*Stamens*.—3 to 4 per flower, conspicuous, emerge from a pistil lode (about 2 mm in length diameter and 137A and 145C in color), filament; 4 mm in length and 145D in color, anthers; 1.5 mm in length, oblong in shape, 146A in color, pollen is abundant in quantity and 8A in color.

*Pistils*.—1, 3-parted, styles; 3, 144A in color, 3 mm in length, stigma; 2-lobed, 145C in color, 1 mm in length and width, ovary; 145A in color and 3.5 mm in length, 2 mm in width.

*Fruit and seed.*—None observed to date.

It is claimed:

1. A new and distinct cultivar of *Buxus* plant named 'JN Select I' as herein illustrated and described.

* * * * *